US009875527B2

(12) United States Patent
Yu et al.

(10) Patent No.: US 9,875,527 B2
(45) Date of Patent: Jan. 23, 2018

(54) APPARATUS AND METHOD FOR NOISE REDUCTION OF SPECTRAL COMPUTED TOMOGRAPHY IMAGES AND SINOGRAMS USING A WHITENING TRANSFORM

(71) Applicant: TOSHIBA MEDICAL SYSTEMS CORPORATION, Otawara-Shi (JP)

(72) Inventors: Zhou Yu, Wilmette, IL (US); Yan Liu, Vernon Hills, IL (US)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 62 days.

(21) Appl. No.: 14/997,365

(22) Filed: Jan. 15, 2016

(65) Prior Publication Data

US 2017/0206635 A1  Jul. 20, 2017

(51) Int. Cl.
G06T 5/00 (2006.01)
G06K 9/52 (2006.01)
G06T 7/00 (2017.01)
G06T 11/00 (2006.01)

(52) U.S. Cl.
CPC .................. *G06T 5/00* (2013.01); *G06K 9/52* (2013.01); *G06T 7/0012* (2013.01); *G06T 11/008* (2013.01); *G06T 2207/10081* (2013.01); *G06T 2207/10116* (2013.01)

(58) Field of Classification Search
None
See application file for complete search history.

(56) References Cited

U.S. PATENT DOCUMENTS

| 8,965,095 B2 | 2/2015 | Zou et al. |
| 2006/0215891 A1 | 9/2006 | Fessler et al. |
| 2011/0268328 A1 | 11/2011 | Bar-Aviv et al. |

(Continued)

FOREIGN PATENT DOCUMENTS

| WO | WO 2011/127609 A1 | 10/2011 |
| WO | WO 2014/172421 A1 | 10/2014 |

OTHER PUBLICATIONS

Mayer, Rulon, Frank Bucholtz, and Dean Scribner. "Object detection by using "whitening/dewhitening" to transform target signatures in multitemporal hyperspectral and multispectral imagery." IEEE transactions on geoscience and remote sensing 41.5 (2003): 1136-1142.*

(Continued)

Primary Examiner — Michelle M Hausmann
(74) Attorney, Agent, or Firm — Oblon, McClelland, Maier & Neustadt, L.L.P.

(57) ABSTRACT

A method and apparatus is provided to denoise material-decomposition data generated using projection data from a spectral computed tomography scanner. A whitening transform is used to transform the material-decomposition data into uncorrelated components and perform denoising on the uncorrelated components. Using different denoising parameters for the various uncorrelated components, a flattening can be achieved for the standard deviation of the noise as a function of X-ray energy, which can be determined using mono-energetic images derived from the material-decomposition data. The whitening transformation and the denoising can be applied the material-decomposition sinograms and/or to material-decomposition images reconstructed from the material-decomposition sinograms.

20 Claims, 17 Drawing Sheets

(56) References Cited

U.S. PATENT DOCUMENTS

| | | | |
|---|---|---|---|
| 2012/0039440 A1 | 2/2012 | Fan et al. | |
| 2013/0051674 A1* | 2/2013 | Goossens | G06T 5/002 382/173 |
| 2014/0005971 A1 | 1/2014 | Roessl et al. | |
| 2014/0185864 A1* | 7/2014 | Halper | G06K 9/0063 382/103 |
| 2014/0369581 A1 | 12/2014 | Fu et al. | |
| 2016/0171648 A1* | 6/2016 | Thibault | G01N 23/046 378/5 |
| 2016/0367212 A1* | 12/2016 | Tang | A61B 6/5288 |

OTHER PUBLICATIONS

Sawatzky, Alex, et al. "Proximal ADMM for multi-channel image reconstruction in spectral X-ray CT." IEEE transactions on medical imaging 33.8 (2014): 1657-1668.*

Wang, Jing, Tianfang Li, and Lei Xing. "Iterative image reconstruction for CBCT using edge-preserving prior." Medical physics 36.1 (2009): 252-260.*

Novak, Leslie M., and Michael C. Burl. "Optimal speckle reduction in polarimetric SAR imagery." IEEE Transactions on Aerospace and Electronic Systems 26.2 (1990): 293-305.*

Choi, Seungjin, and Andrzej Cichocki. "Blind separation of nonstationary and temporally correlated sources from noisy mixtures." Neural Networks for Signal Processing X, 2000. Proceedings of the 2000 IEEE Signal Processing Society Workshop. vol. 1. IEEE, 2000.*

Torres, Sebastián M., Christopher D. Curtis, and J. R. Cruz. "Pseudowhitening of weather radar signals to improve spectral moment and polarimetric variable estimates at low signal-to-noise ratios." IEEE transactions on geoscience and remote sensing 42.5 (2004): 941-949.*

Wang, Jui Teng. "Decorrelation based receive transformation for MIMO system under multi-user co-channel interference." IEEE Wireless Communications Letters 3.3 (2014): 305-308.*

Liu, et al., "A joint iterative reconstruction algorithm for dual energy CT using ADMM", The 13$^{th}$ International Meeting on Fully Three-Dimensional Image Reconstruction in Radiology and Nuclear Medicine, pp. 511-pp. 514.

Liu, et al., "Impact of covariance modeling in dual-energy spectral CT image reconstruction", 2015, Proc. of SPIE vol. 9412, 94123Q.

Zhang, et al., "Model-Based Iterative Reconstruction for Dual-Energy X-Ray CT Using a Joint Quadratic Likelihood Model", 2013, IEEE.

Long, et al., "Multi-Material Decomposition Using Statistical Image Reconstruction for Spectral CT", IEEE Transaction on Medical Imaging, vol. 33, No. 8, Aug. 2014.

Alvarez, et al., "Dimensionality and noise in energy selective x-ray imaging", 2013, Med Physics Nov. 2013; 40(11): 111909. http://www.ncbi.nlm.nih.gov/pmc/articles/PMC3808483/.

* cited by examiner

APPARATUS AND METHOD FOR NOISE REDUCTION OF SPECTRAL COMPUTED TOMOGRAPHY IMAGES AND SINOGRAMS USING A WHITENING TRANSFORM

FIELD

This disclosure relates to denoising material decompositions and images generated from spectral computed tomography (CT) projection data, and, more particularly, to denoising material decompositions and images using a whitening transform.

BACKGROUND

Computed tomography (CT) systems and methods are widely used, particularly for medical imaging and diagnosis. CT systems generally create images of one or more sectional slices through a subject's body. A radiation source, such as an X-ray tube, irradiates the body from one side. A collimator can limit the angular extent of the X-ray beam, so that radiation impinging on the body is substantially confined to a planar region defining a cross-sectional slice of the body. At least one detector on the opposite side of the body receives radiation transmitted through the body substantially in the plane of the slice. The attenuation of the radiation that has passed through the body is measured by processing electrical signals received from the detector.

A CT sinogram indicates attenuation through the body as a function of "space" along a detector array and "time/angle" of a scan of measurements performed at a series of projection angles. The space dimension refers to the position along a one-dimensional array of X-ray detectors. The time/angle dimension refers to the projection angle of X-rays changing as a function of time, such that as time progresses the projection angle increments and projection measurements are performed at a linear succession of projection angles. The attenuation resulting from a particular volume (e.g., a vertebra) will trace out a sine wave around the vertical axis—volumes farther from the axis of rotation having sine waves with larger amplitudes, the phase of a sine wave determining the volume's angular position around the rotation axis. Performing an inverse Radon transform or equivalent image reconstruction method reconstructs an image from the projection data in the sinogram—the reconstructed image corresponding to a cross-sectional slice of the body.

Conventionally, energy-integrating detectors have been used to measure CT projection data. Now, recent technological developments are making photon-counting detectors a feasible alternative to conventional energy-integrating detectors. Photon-counting detectors have many advantages, including their capacity for performing spectral CT. To obtain the spectral nature of the transmitted X-ray data, the photon-counting detectors split the X-ray beam into its component energies or spectrum bins and count a number of photons in each of the bins. Since spectral CT involves the detection of transmitted X-rays at two or more energy levels, spectral CT generally includes dual-energy CT by definition. Due to different materials exhibiting different spectral attenuation of the X-rays, projection data from spectral CT can be decomposed into material components using a material decomposition. The material-component images can then be reconstructed from material-component sinograms.

One result of this material decomposition of spectrally resolved projection data is that strong noise correlations are introduced among the material-component sinograms and material-component images. The correlations of the noise can be used to denoise in order to improve image quality of the reconstructed images. Denoising reconstructed material images is desirable to enhance the diagnostic quality of these images. Conventional methods of denoising material-component images either are computationally intensive or do not utilize the correlated nature of the noise to improve denoising.

BRIEF DESCRIPTION OF THE DRAWINGS

A more complete understanding of this disclosure is provided by reference to the following detailed description when considered in connection with the accompanying drawings, wherein.

DETAILED DESCRIPTION

Figure 1:
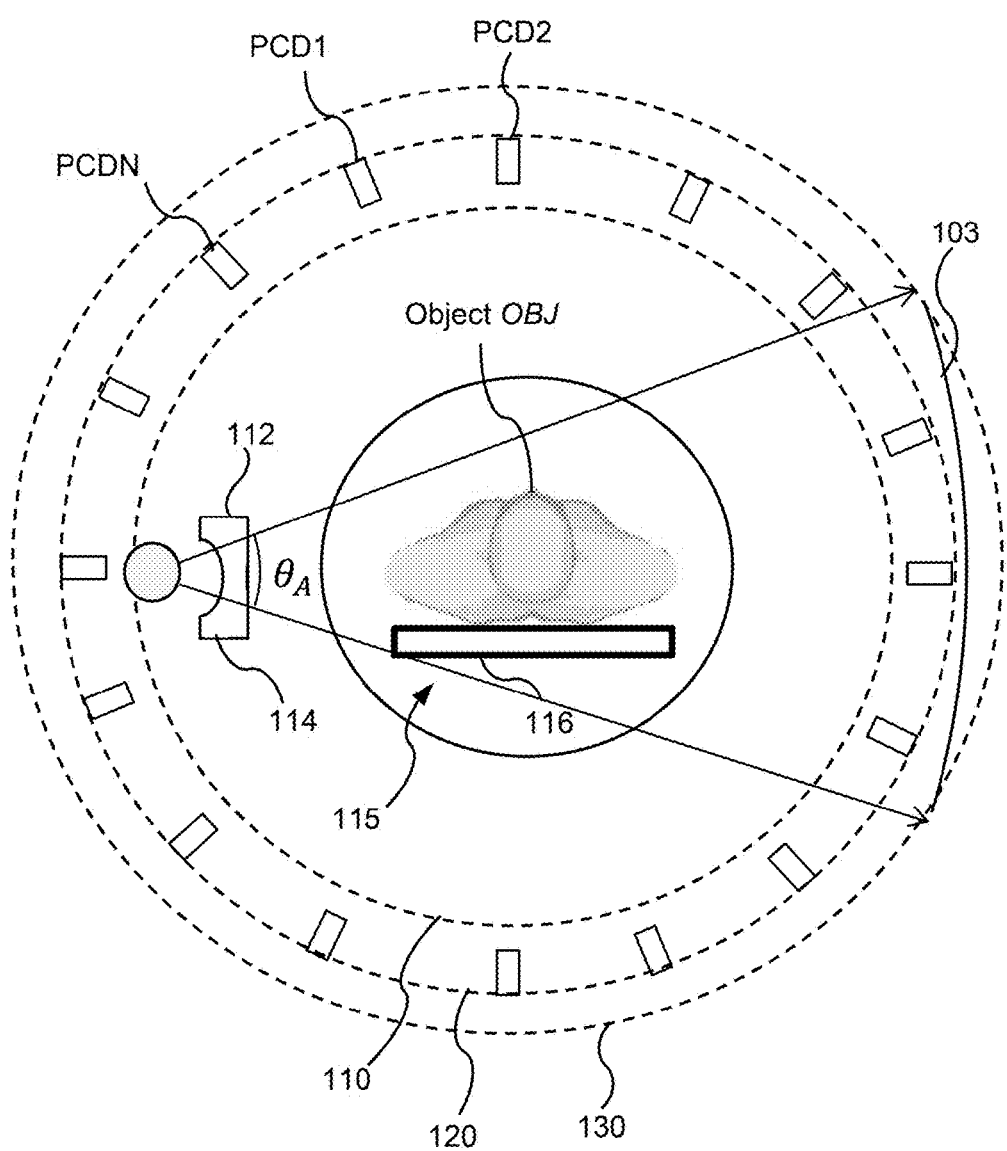
FIG. 1 shows a schematic of an implementation of an arrangement of X-ray source and X-ray detectors for a CT scanner.

Spectral computed tomography (CT) technology has shown the potential to provide material characterization and precise quantitative information for diagnosis. In the implementation of spectral CT, material components are decomposed from various spectral absorption measurements along the same X-ray trajectories. One result of this material decomposition is that strong noise correlations are introduced in both material sinograms and material images. Herein, the phrase "material-component" is often abbreviated to "material" where the meaning is clear.

Determining a correlated noise model in statistical-based denoising algorithms can advantageously be used to improve image quality. However, directly modeling noise covariance as a weighting matrix in the cost function is challenging for conventional parallel computing algorithms and requires large computational resources. Moreover, the noise of mono-energetic images is keV dependent and hard to control using conventional denoising frameworks. Accordingly, the methods described herein achieve improved image quality by using statistical information from the images while being more computationally efficient than conventional methods.

The methods described herein provide noise reduction for spectral CT by using a whitening transform. Compared to the conventional denoising method, the methods described herein model the noise covariance model in the cost function to improve image quality. Compared to the statistical based iterative image reconstruction method with covariance modelling, the new method requires less computational time. Moreover, the methods described herein can control the mono-energetic noise and can produce reconstructed images and sinogram data having noise characteristics that are more uniform as a function of X-ray energy.

Both spectral CT image denoising and sinogram denoising can be used to recover a material-component signal $\hat{y}$ from a noisy measurement y. To perform denoising effectively, a denoising method reduces the noise in the spectral CT image or sinogram while simultaneously preserving textures and edges corresponding to the desired signal. For example, denoising can be achieved by solving the noise reduction problem to minimize a penalized weighted least square (PWLS) term cost function, which can be given by $$\min_{\hat{y}} \frac{1}{2}(y-\hat{y})^T \Sigma_y^{-1}(y-\hat{y}) + \beta R(\hat{y}),$$

wherein $\Sigma_y^{-1}$ is an inverse covariance matrix of the measurements y, $\beta$ is a regularization parameter to control the denoising strength, and $R(\hat{y})$ denotes regularization from prior information.

However, accurately estimating the covariance $\Sigma_y$ can be difficult for spectral CT images. To overcome the challenges of denoising using the PWLS cost function on the measurements y of the combined material-basis components, the methods described herein provide denoising without requiring an accurate covariance model and can be easily solved by conventional parallel computing algorithms.

The methods described herein use a whitening transform to de-correlate the noisy signals by transforming into mutually uncorrelated orthonormal bases. Next, the noise reduction problem is solved for each uncorrelated orthonormal basis before using an inverse whitening transform to transform back to the material bases. A whitening transform matrix can advantageously be calculated from the covariance matrix by eigenvalue decomposition.

Referring now to the drawings, wherein like reference numerals designate identical or corresponding parts throughout the several views, FIG. 1 shows source and detector portions of a computed tomography (CT) scanner having both energy-integrating detectors arranged in a third-generation geometry and photon-counting detectors arranged in a fourth-generation geometry. Illustrated in FIG. 1 is an implementation for placing the photon-counting detectors (PCDs) in a predetermined fourth-generation geometry in combination with a detector unit 103 in a predetermined third-generation geometry in a CT scanner system. The diagram illustrates relative positions among an object OBJ to be scanned resting on a table 116, an X-ray source 112, a collimator/filter 114, an X-ray detector 103, and photon-counting detectors PCD1 through PCDN.

In one implementation, the X-ray source 112, the collimator/filter 114 are fixedly connected to a rotational component 110 that is rotatably connected to a gantry, and the PCDs are fixedly connected to a circular component 120 that is fixedly connected to the gantry. The gantry of the CT scanner also includes an open aperture 115 enabling the object OBJ to be placed in a projection plane of the X-rays from the X-ray source. The X-ray detector 103 is fixedly connected to a rotational component 130 that is rotatably connected to the gantry. The rotational component 120 and the rotational component 130 can rotate in unison maintaining the X-ray detector 103 diametrical opposed to the X-ray source 112 to obtain projection data of the object OBJ at a progression of projection angles. Sinograms are created by arranging the projection data with projection angles arranged along one axis and the spatial dimensions of the projection data arranged along the other axes.

In spectral CT, radiation having multiple energy components is used to make projective measurements of the object OBJ. These projective measurements are made at a series of angles enabling conventional CT image reconstruction methods similar to non-spectral CT. However, unlike non-spectral CT, spectral CT generates additional information (i.e., spectral attenuation information) enabling a decomposition of the projective measurements into material components, usually two material components. The material decomposition results in two component materials because there are two dominant interaction mechanisms causing the attenuation of the X-ray beams traversing the imaged object OBJ. These interaction mechanisms are Compton scattering and photoelectric absorption. Mapping the projection data from the spectral domain to the material domain can be performed either before or after the image reconstruction process. However, performing material decomposition from the spectral domain to the material domain before the reconstruction process is preferable due to beam hardening considerations. Herein, we are concerned with performing the material decomposition before the image reconstruction process.

When most of the X-rays have energies well above the K-edge of the majority atoms of the imaged object OBJ, as is the case for conventional X-ray sources imaging biological objects, the material decomposition problem can be solved using only two energy components consistent with the existence of the two dominant interaction processes discussed above. Thus, spectral CT is sometimes referred to as dual-energy CT, and the material decomposition process can be referred to as dual-energy analysis. Herein, spectral CT will include at least dual-energy CT, but also includes projective measurements with more than two energy components, such that the two-material decomposition problem is overdetermined. As discussed in U.S. patent application Ser. No. 13/906,110, incorporated herein by reference in its entirety, the additional information provided by more energy components can be used effectively in noise balancing and related methods to improve image quality. Further, the nonlinear detector response of the PCDs can be calibrated and corrected, as discussed in U.S. patent application Ser. No. 14/676,594, incorporated herein by reference in its entirety.

A dual-energy analysis method can be used because the attenuation of X-rays in biological materials is dominated by two physical processes (i.e., photoelectric absorption and Compton scattering). Thus, the attenuation coefficient as a function of energy can be approximated by the decomposition $$\mu(E,x,y)=\mu_{PE}(E,x,y)+\mu_C(E,x,y),$$

wherein $\mu_{PE}(E,x,y)$ is the photoelectric attenuation and $\mu_C(E,x,y)$ is the Compton attenuation. Alternatively, this attenuation coefficient can be rearranged into a decomposition of a high-Z material (i.e., material 1) and a low-Z material (i.e., material 2) to become $$\mu(E,x,y)=\mu_1(E)c_1(x,y)+\mu_2(E)c_2(x,y),$$

wherein $c_1(x,y)$ and $c_2(x,y)$ are, respectively, the first and second basis images.

The detected spectrum is given by $$S(E_i)=S_{air}(E_i)\exp[-\mu_1(E_i)L_1-\mu_2(E_i)L_2],$$

wherein the attenuation coefficients $\mu_1$ and $\mu_2$ are known functions of the X-ray energy, and the spectrum $S_{air}$, corresponding to the X-rays propagating through air in the absence of an absorptive object OBJ, is also known based on previous calibrations, for example. This detected spectrum can be coarse grained into X-ray energy bins (e.g., five energy bins can be used, each covering a respective energy sub-band, such that combined the energy bins span an energy spectrum from approximately 20 keV to approximately 160 keV). The count value $N_m$ of the $m^{th}$ energy bin can be given by $$N_m=\int dE w_m(E)S(E),$$

wherein $w_m(E)$ is a windowing function corresponding to the energy sub-band of the $m^{th}$ energy bin. For each energy bin and projection angle, a projection image is acquired $N_m(X_i)$, wherein $X_i$ is the position along the X-ray detector corresponding to the $i^{th}$ pixel of the detector. The combination of all the projection images for a given energy bin and corresponding to a series of projection angles is the projection data g for that energy bin.

When at least two energy bins are detected for each pixel, the projection lengths $L_1(X_i)$ and $L_2(X_i)$ for each pixel of a projection image, can be estimated using the above expressions for the detected energy spectrum and the number of counts in each energy bin. The transformation from energy resolved X-ray counts to projection lengths corresponding to the first and second material components is referred to as a material decomposition.

Figure 2:
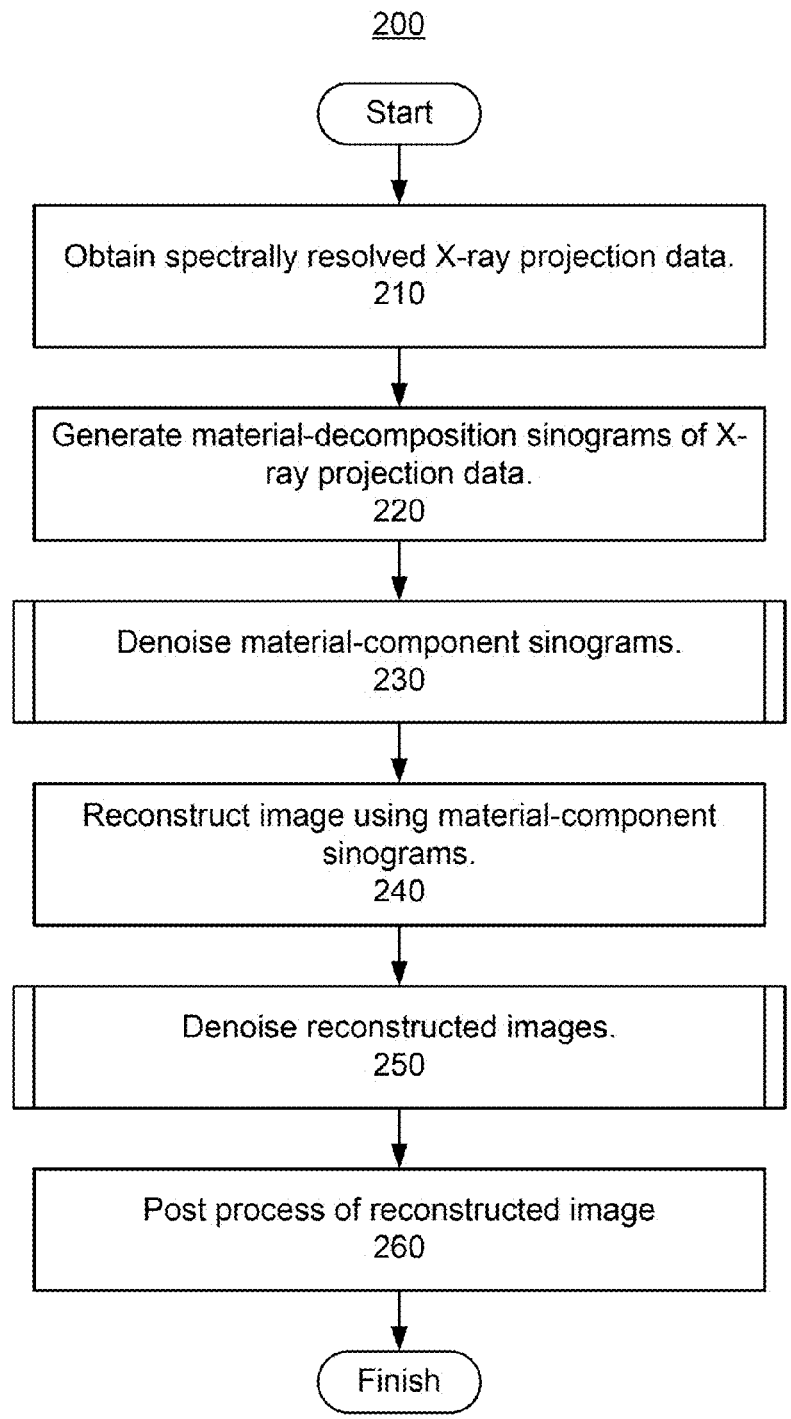
FIG. 2 shows a flow diagram of a method of reconstructing denoised material-component CT images.

FIG. 2 shows a flow diagram of method 200 that reconstructs a denoised image using spectral CT.

Figure 14:
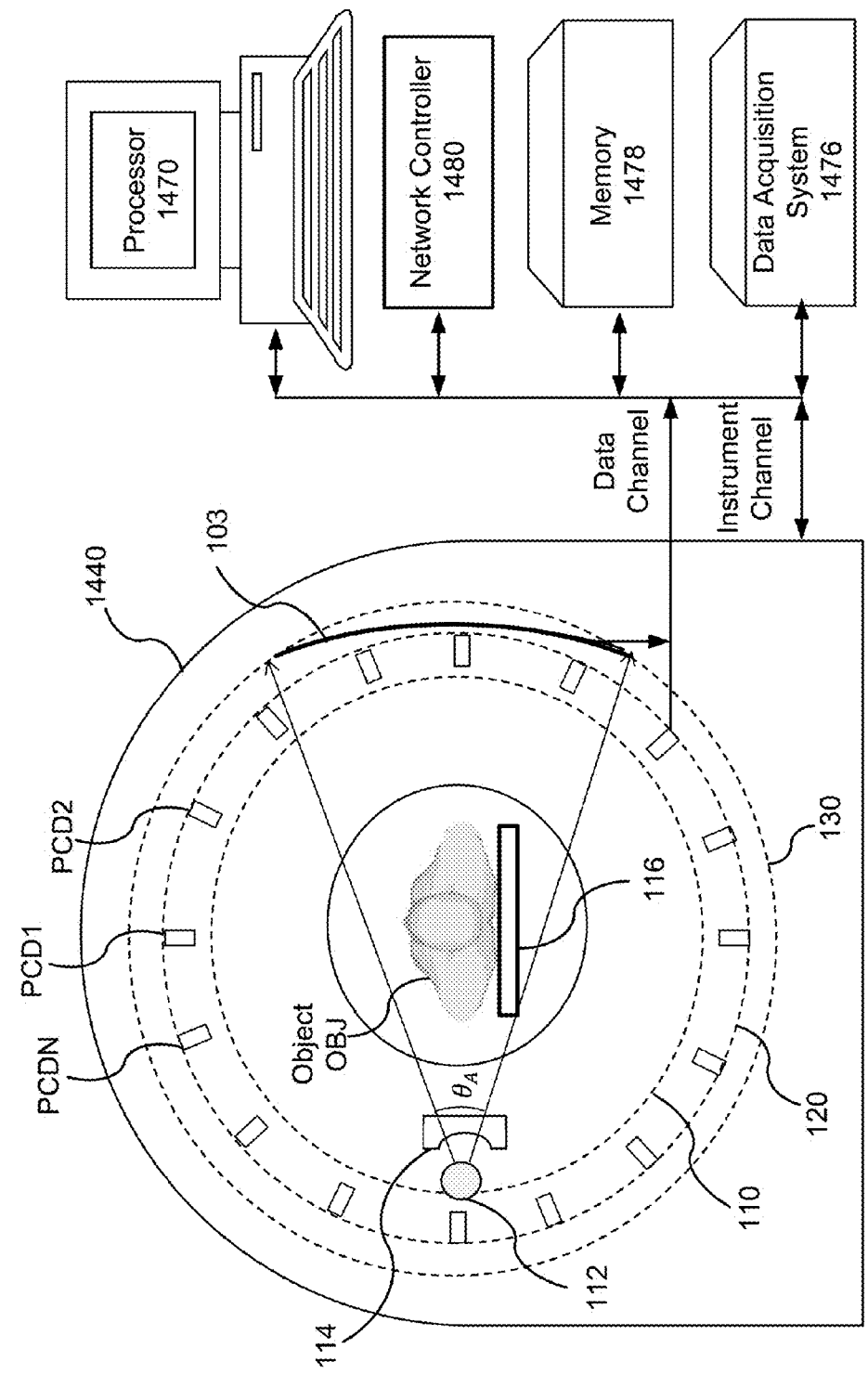
FIG. 14 shows a schematic of an implementation of a CT scanner.

In step 210 of method 200, spectrally resolved X-ray projection data is obtained. For example, FIGS. 1 and 14 show a CT scanner that can be used to obtain the X-ray projection data. Further, the X-ray projection data can be stored and retrieved from a computer readable memory.

In step 220 of method 200, projection lengths $L_1$ and $L_2$ are determined from the projection data. For example, the projection lengths can be determined using any of the methods given in U.S. patent application Ser. No. 13/906,110, patent application Ser. No. 14/676,594, U.S. patent application Ser. No. 14/593,818, and U.S. patent application Ser. No. 14/603,135, each incorporated herein by reference in its entirety.

In process 230 of method 200, the material-component sinograms are denoised.

In step 240 of method 200, material-component images are reconstructed from the material-component sinograms. For example, the images can be reconstructed using one of a filtered back-projection method, an iterative reconstruction method (e.g., the algebraic reconstruction technique (ART) method and the total variation minimization regularization methods), Fourier-transform-based method (e.g., direct Fourier method), and statistical method (e.g., maximum-likelihood expectation-maximization algorithm based methods).

In process 250 of method 200, material-component images are denoised. In certain implementations, process 250 can be performed and process 230 omitted. Alternatively, process 230 can be performed and process 250 omitted. Further, in certain implementations, both process 250 and process 230 can be performed.

In step 260 of method 200, post processing of the material-component images can be performed. For example, mono-energetic images can be constructed from the material-component images and the attenuation coefficients $\mu_1(E)$ and $\mu_2(E)$.

Figure 3A:
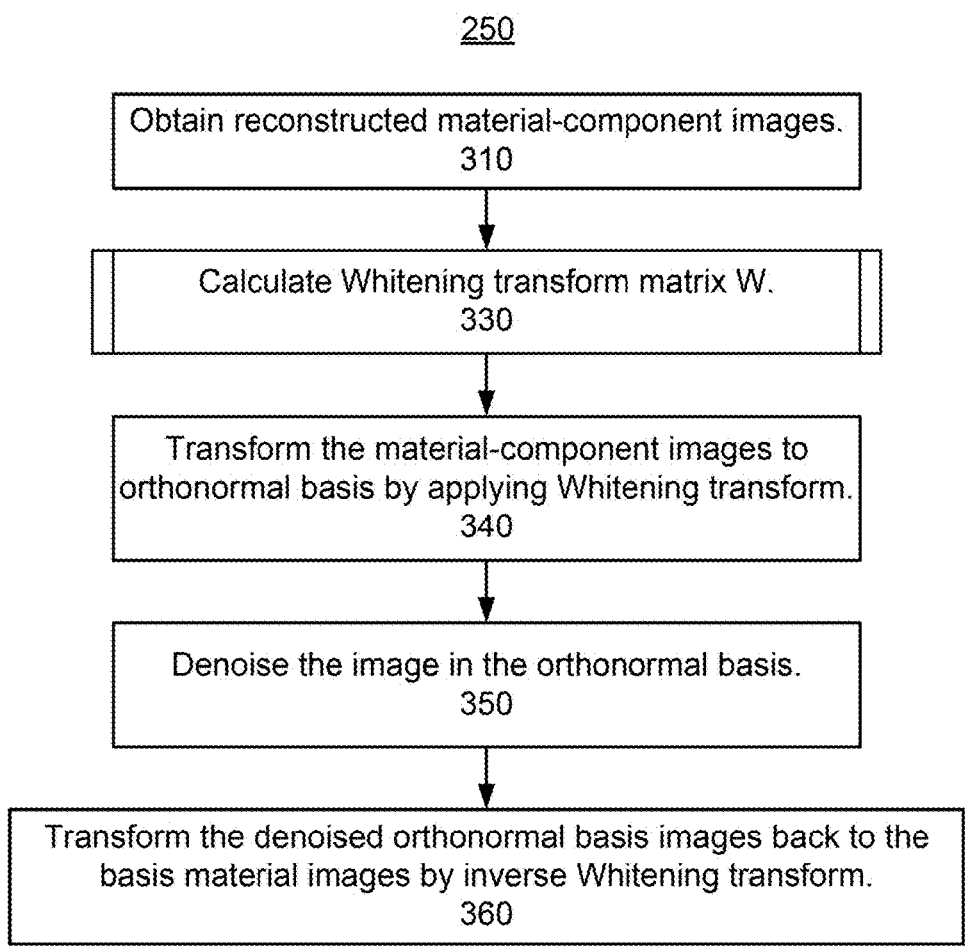
FIG. 3A shows a flow diagram of a process to denoise reconstructed images using a whitening transform.

FIG. 3A shows a flow diagram of process 250, according to one implementation.

In step 310 of method 250, the material-component images are obtained.

In process 330 of method 250, a whitening transform W is calculated.

Figure 3B:
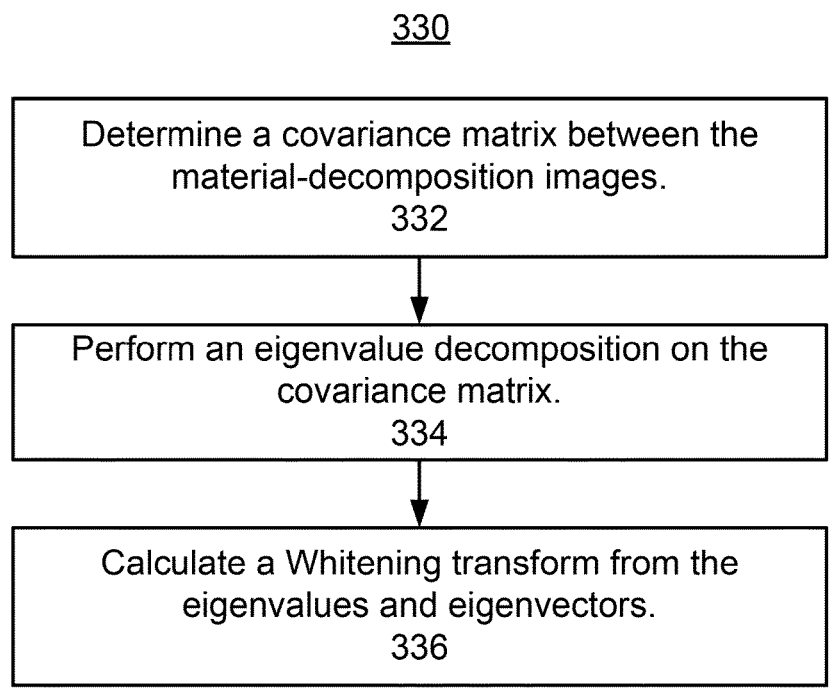
FIG. 3B shows a flow diagram of a process to calculate a whitening transform matrix.

FIG. 3B shows a flow diagram of the process 330.

In step 332 of process 330, a covariance matrix is determined between patches of the reconstructed images of the first and second material components. For example, if the reconstructed images corresponding to the first and second material-components are respectively given by $RI^{(1)}(i,j,k)$ and $RI^{(2)}(i,j,k)$, wherein i=1, 2 ... $N_i$, j=1, 2 ... $N_j$, and k=1, 2 ... $N_k$ are the indices of the images, then a covariance matrix between patches corresponding to indices $i_1 \leq i \leq i_2$, $j_1 \leq j \leq j_2$, and $k_1 \leq k \leq k_2$ is given by $$\Sigma_{\hat{\alpha}} = \Sigma_{nm} = \begin{bmatrix} s_{11} & s_{12} \\ s_{21} & s_{22} \end{bmatrix},$$

wherein the matrix elements are calculated using the expectation values of the mean subtracted products, which can be calculated as $$s_{nm} = \sum_{i=i_1}^{i_2} \sum_{j=j_1}^{j_2} \sum_{k=k_1}^{k_2} (RI^{(n)}(i,j,k) - \mu_n)(RI^{(m)}(i,j,k) - \mu_m),$$

and the mean is given by $\mu_n = RI^{(n)}(i,j,k)$.

Alternatively, a covariance matrix $\Sigma_{\tilde{x}}$ can be calculated between reconstructed images for each of the energy bins and a transformation can be performed on the energy-bin covariance matrix $\Sigma_{\tilde{x}}$ to generate the material-component covariance matrix $\Sigma_{\hat{\alpha}}$. The transformation from the energy-bin covariance matrix $\Sigma_{\tilde{x}}$ to the material-component covariance matrix $\Sigma_{\hat{\alpha}}$ can be given by $\Sigma_{\hat{\alpha}} = K \Sigma_x K^T$ wherein the elements of the matrix K are given by $K_{i,j} = \int_E q_i(E) f_j(E) dE$, $f_j(E)$ denotes the energy dependent material attenuation coefficients, $$q_i(E) = \frac{S(E)D(E)}{\int_E S(E)D(E)dE}$$

is the system weighting function which can be calculated from the energy spectra S(E) and detector response D(E).

In step 332 of process 330, the covariance matrix $\Sigma_{\hat{\alpha}}$ is decomposed into its eigenvalues (represented by the diagonal matrix $\Lambda$) and eigenvectors (represented by the columns of matrix $\Phi$). Using the covariance matrix $\Sigma_{\hat{\alpha}}$ the eigenvalues and eigenvectors can be obtained by solving the equation $\Sigma_{\hat{\alpha}} \Phi = \Phi \Lambda$ wherein the matrix $\Phi$ is a transform matrix to diagonalize the covariance matrix $\Sigma_{\hat{\alpha}}$, the columns of $\Phi$ are the eigenvectors of the covariance matrix, and $\Lambda$ is a diagonal matrix having the eigenvalues as its diagonal elements.

In step 340 of method 250, the whitening transform is calculated as $W = \Lambda^{-1/2} \Phi^T$, and the material-component images $RI^{(m)}(i,j,k)$ can be transformed to uncorrelated-basis images $U^{(m)}(i,j,k)$ according to $$\begin{bmatrix} U^{(1)}(i,j,k) \\ U^{(2)}(i,j,k) \end{bmatrix} = \begin{bmatrix} W_{11} & W_{12} \\ W_{21} & W_{22} \end{bmatrix} \begin{bmatrix} RI^{(1)}(i,j,k) \\ RI^{(2)}(i,j,k) \end{bmatrix}.$$

In step 350 of method 250, denoising is applied to the uncorrelated-basis images $U^{(m)}(i,j,k)$. For example, the images $U^{(1)}$ and $U^{(2)}$ can be denoised using low-pass filtering, wherein the images $U^{(1)}$ and $U^{(2)}$ are respectively filtered using different low-pass filter parameters.

In certain implementations, the uncorrelated-basis images can be denoised using an iterative denoising algorithm such as PWLS algorithm by iteratively solving $$\min_{\hat{U}^{(m)}} \left\{ \left(U^{(m)} - \hat{U}^{(m)}\right)^T D^{-1} \left(U^{(m)} - \hat{U}^{(m)}\right) + \beta_m R(\hat{U}^{(m)}) \right\} \; m = 1, 2$$

wherein $D^{-1}$ is a diagonal matrix and could be any statistical weighting matrix, $\beta_1$ and $\beta_2$ are two parameters controlling the regularization strengths of the denoised images $\hat{U}^{(1)}$ and $\hat{U}^{(2)}$ in the uncorrelated basis.

In certain implementations, an isotropic quadratic regularization can be used such that the regularization terms is given by the function $R(\hat{U}^{(m)}) = \hat{\Delta}_{(m)}^2$.

wherein $\hat{\Delta}_{(1)}$ and $\hat{\Delta}_{(2)}$ are the nearby pixels differences of the denoised images $\hat{U}^{(1)}$ and $\hat{U}^{(2)}$ in the orthonormal bases.

In certain implementations, an anisotropic quadratic regularization can be used such that the regularization terms is given by the function $R(\hat{U}^{(m)}) = \exp(-(\Delta_{(m)}/\delta_{(m)})^2) \hat{\Delta}_{(m)}^2$.

wherein $\hat{\Delta}_{(1)}$ and $\hat{\Delta}_{(2)}$ are the nearby pixels differences of the denoised images $\hat{U}^{(1)}$ and $\hat{U}^{(2)}$ in the orthonormal bases, $\Delta_{(1)}$ and $\Delta_{(2)}$ are the nearby pixels differences from input image $U^{(1)}$ and $U^{(2)}$ (e.g., the noisy data), and $\delta_{(1)}$ and $\delta_{(2)}$ are edge preserving parameters corresponding to the two uncorrelated bases.

Additional, many spatial-domain denoising methods can be applied to the images in the uncorrelated basis, including: linear smoothing filters, anisotropic diffusion, non-local means, and nonlinear filters.

Linear smoothing filters remove noise by convolving the original image with a mask that represents a low-pass filter or smoothing operation. For example, the Gaussian mask comprises elements determined by a Gaussian function. This convolution brings the value of each pixel into closer agreement with the values of its neighbors. In general, a smoothing filter sets each pixel to the average value, or a weighted average, of itself and its nearby neighbors; the Gaussian filter is just one possible set of weights. Disadvantageously, smoothing filters tend to blur an image because pixel intensity values that are significantly higher or lower than the surrounding neighborhood are smeared or averaged across their neighboring area. Sharp boundaries become fuzzy. Generally, local linear filter methods assume the homogeneity could be found in the local neighbourhood are homogeneous and therefore tend to impose homogeneity on the image obscuring non-homogeneous features, such as lesions or organ boundaries.

Anisotropic diffusion removes noise while preserving sharp edges by evolving an image under a smoothing partial differential equation similar to the heat equation. If the diffusion coefficient were a spatially constant, this smoothing would be equivalent to linear Gaussian filtering, but when the diffusion coefficient is anisotropic according to the presence of edges, the noise can be removed without blurring the edges of the image.

A median filter is an example of a nonlinear filter and, if properly designed, a nonlinear filter can also preserve edges and avoid blurring. A median filter operates, for example, by evaluating each pixel in the image, sorting the neighboring pixels according to intensity, and replacing the original value of the pixel with the median value from the ordered list of intensities. The median filter is one example of a rank-conditioned rank-selection (RCRS) filter. For example, median filters and other RCRS filters can be applied to remove salt and pepper noise from an image without introducing significant blurring artifacts.

In non-local means filtering, rather than performing a weighted average of pixels according to their spatial proximity, pixels are determined to be a weighted average according to the similarity between patches within the images. Thus, noise is removed based on non-local averaging of all the pixels in an image—not just the neighboring pixels. In particular, the amount of weighting for a pixel is based on the degree of similarity between a small patch centered near that pixel and another small patch centered around the pixel being denoised.

In step 360 of method 250, the denoised images in the uncorrelated basis are transformed back into the material-component basis using an inverse of the whitening transform.

The whitening transform and inverse whitening transform can each be performed on patches of the total image, rather than being performed on the total image. Thus, the whitening transform can be spatial variant across the image. Further, the process 330 and steps 340, 350, and 360 can be performed piecewise on patches of the material-component images.

Figure 3C:
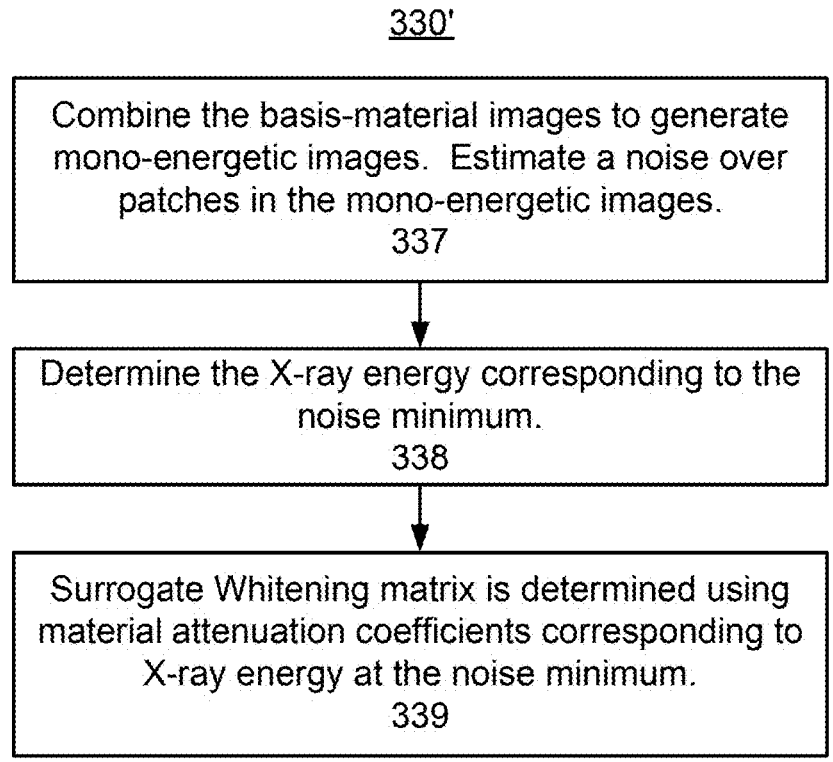
FIG. 3C shows a flow diagram of a process to calculate a surrogate whitening transform matrix.

As an alternative to the whitening matrix W determined using process 330 shown in FIG. 3B, a Surrogate whitening transform can be calculated using process 330' shown in FIG. 3C. Thus, process 250 can be performed using process 330' instead of process 330.

In step 337 of process 330', the material-component basis images are combined to generate mono-energetic images within a clinically relevant range of X-ray energies (e.g., the range from approximately 20 keV to 140 keV).

Figure 4A:
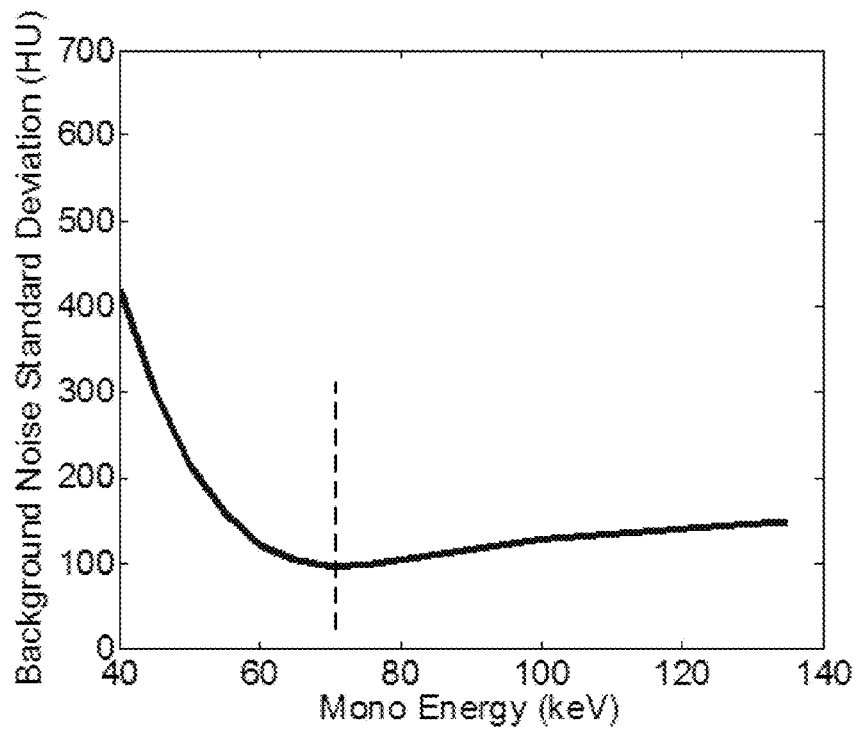
FIG. 4A shows a plot of a background noise standard deviation of mono-energetic images as a function of X-ray.

In step 338 of process 330', using small patches, a standard deviation is calculated for each mono-energetic images to generate a curve representing the background noise standard deviation as a function of the X-ray energy. This curve is then used to determine the X-ray energy corresponding to the lowest value of the curve. For example, FIG. 4A shows an example curve representing the background noise standard deviation, and the X-ray energy $E_{min}$ corresponding to the minimum noise is indicated by the vertical dashed line shown on FIG. 4A.

Figure 4B:
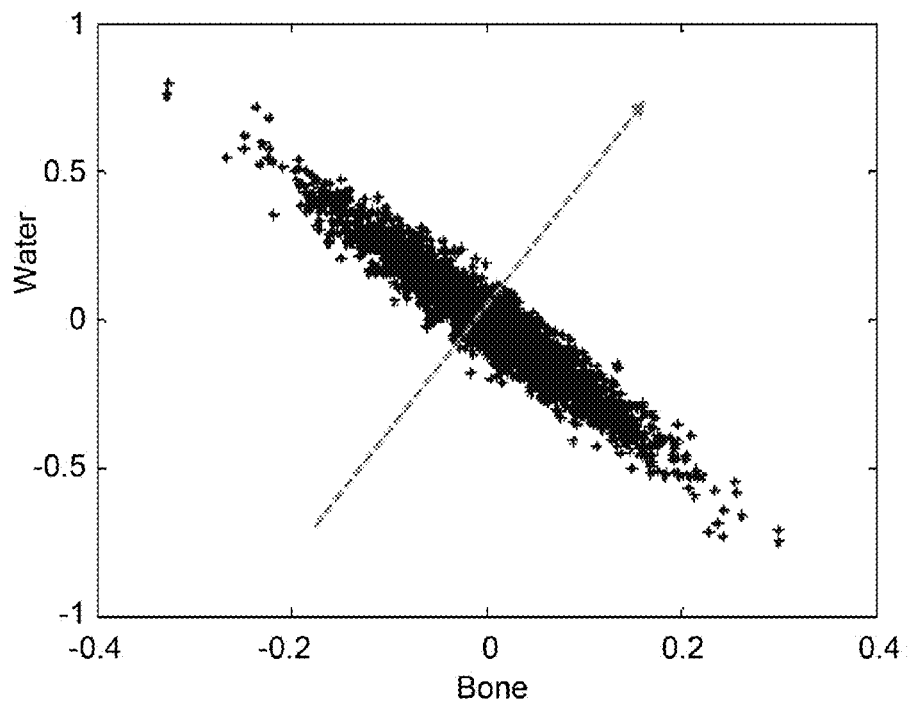
FIG. 4B shows a scatter plot of a correlation between a bone material image and a muscle (water) material image.
Figure 4C:
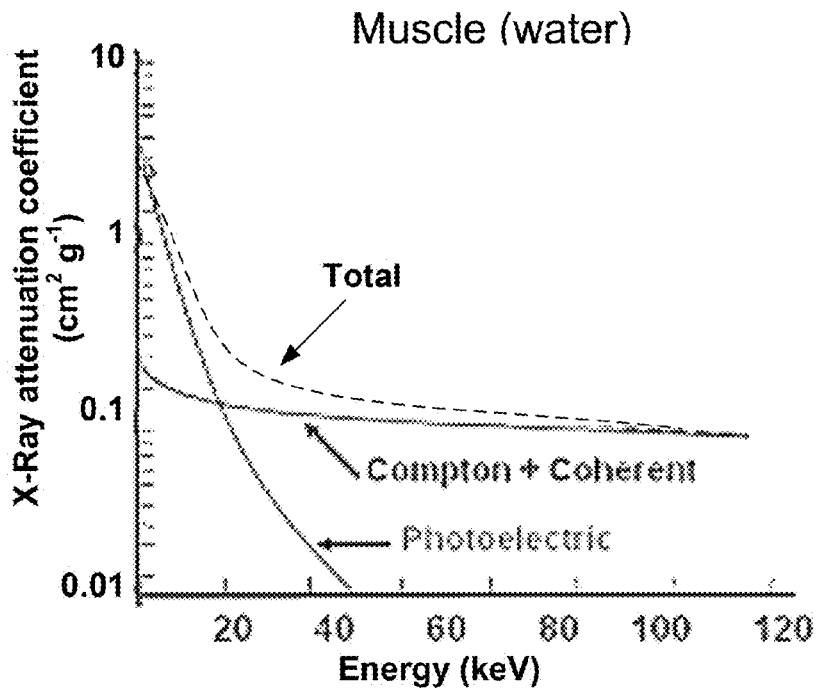
FIG. 4C shows an example of a plot of an absorption coefficient of muscle (water) as a function of X-ray energy.
Figure 4D:
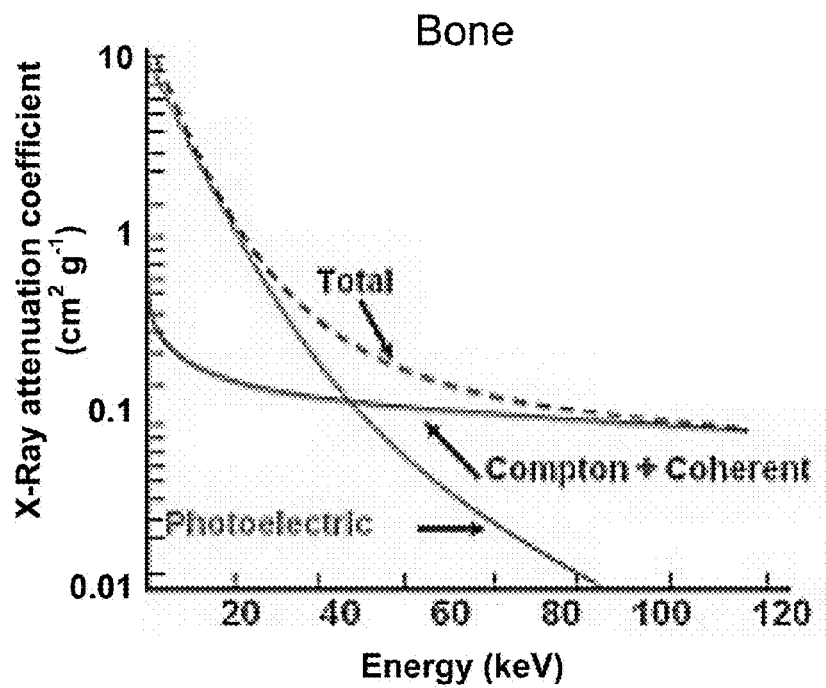
FIG. 4D shows an example of a plot of an absorption coefficient of bone as a function of X-ray energy.
Figure 5:
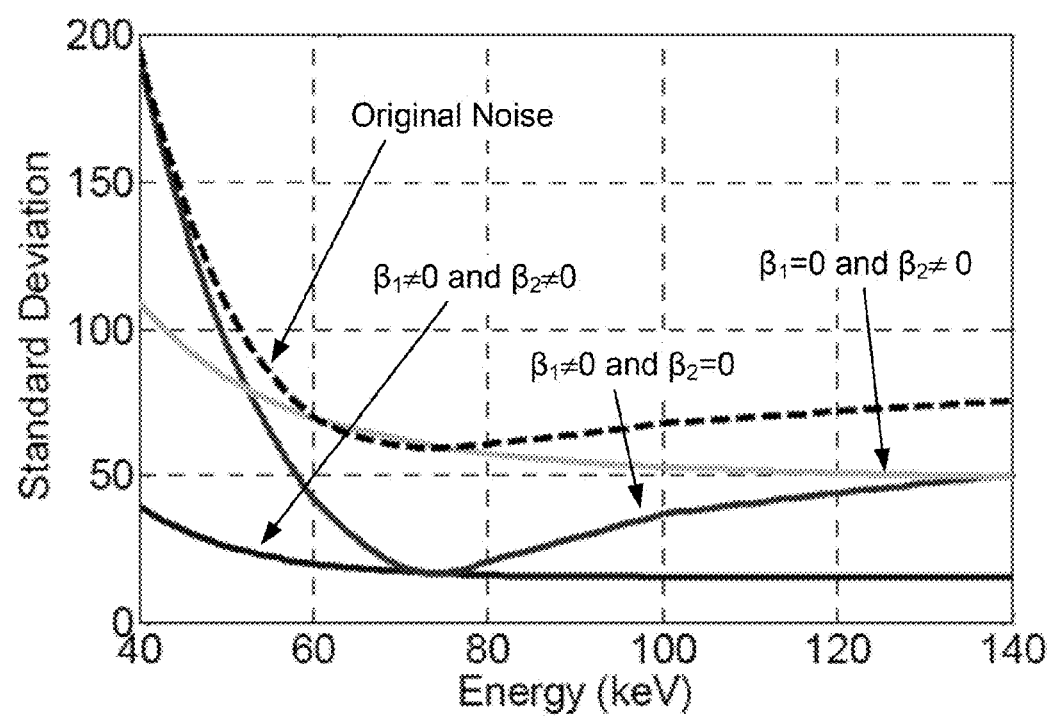
FIG. 5 shows a plot of the background noise standard deviation of mono-energetic images after various types of denoising have been performed in the uncorrelated bases.

FIG. 4B shows a cluster plot of zero-mean material-component images using bone and water as the first and second materials, wherein, for each pixel, the pixel value for the water image determines a value along the vertical axis and the corresponding pixel value for the bone image determines a value along the horizontal axis. The axis in FIG. 4B corresponding to the dashed grey arrow is directed along the direction of the eigenvector corresponding to the smallest eigenvalue of the covariance matrix, and this direction can be estimated using the first and second absorption coefficients $\mu_1(E_{min})$ and $\mu_2(E_{min})$ at the X-ray energy $E_{min}$ corresponding to the noise minimum in FIG. 4A. FIGS. 4C and 4D show examples of absorption coefficients $\mu_1(E)$ and $\mu_2(E)$ for muscle (water) and bone respectively. Thus, using FIGS. 4A, 4C, and 4D the values of absorption coefficients $\mu_1(E_{min})$ and $\mu_2(E_{min})$ at the X-ray energy $E_{min}$ can be determined.

In step 339 of process 330', a Surrogate whitening transform is given by $$W_{Surr} = \alpha \begin{pmatrix} \mu_1(E_{min}) & \mu_2(E_{min}) \\ -\mu_2(E_{min}) & \mu_1(E_{min}) \end{pmatrix},$$

wherein $\alpha$ is a normalization parameter.

FIG. 6 shows a plot of the standard deviation of mono-energetic images as a function of energy for four scenarios: (1) original noise—showing the standard deviation without denoising the image; (2) $\beta_1 \neq 0$ and $\beta_2 \neq 0$—both uncorrelated bases after the whitening transform are denoised; (3) $\beta_1 \neq 0$ and $\beta_2 = 0$—only the uncorrelated basis corresponding to the larger eigenvalue is denoised; and (4) $\beta_1 \neq 0$ and $\beta_2 \neq 0$—only the uncorrelated basis corresponding to the smaller eigenvalue is denoised.

The standard deviation curve for the unfiltered images has a concave shape. This concave shape is compounded when only the uncorrelated basis image corresponding to the larger eigenvalue is denoised, and the concave shape is flattened when only the uncorrelated basis image corresponding to the smaller eigenvalue is denoised. Through the choice of the relative values of the regularization parameters $\beta_1$ and $\beta_2$ the standard deviation curve can be flattened while also reducing the standard deviations corresponding to all X-ray energies, as indicated by the curve for $\beta_1 \neq 0$ and $\beta_2 \neq 0$.

Figure 6A:
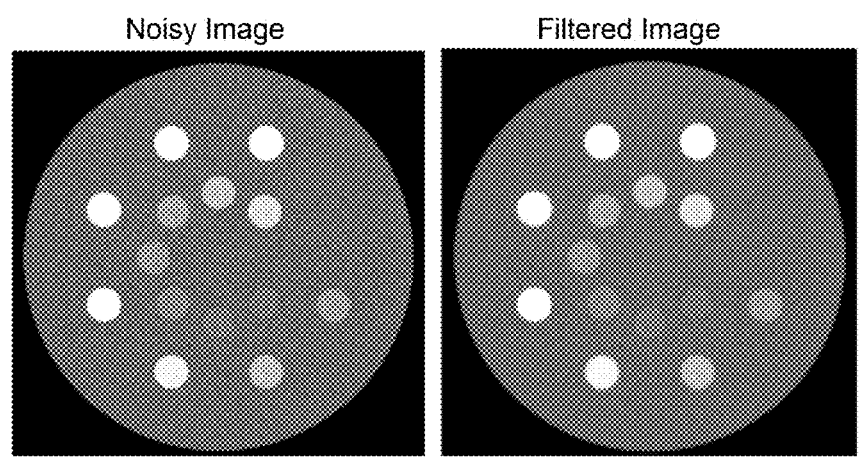
FIG. 6A shows noisy and filtered images in the uncorrelated basis corresponding to the smaller eigenvalue of the covariance matrix, according to an isotropic denoising implementation.

FIG. 6A shows simulated results for a first material basis of a noisy image and a filtered image, using an isotropic quadratic regularization.

Figure 6B:
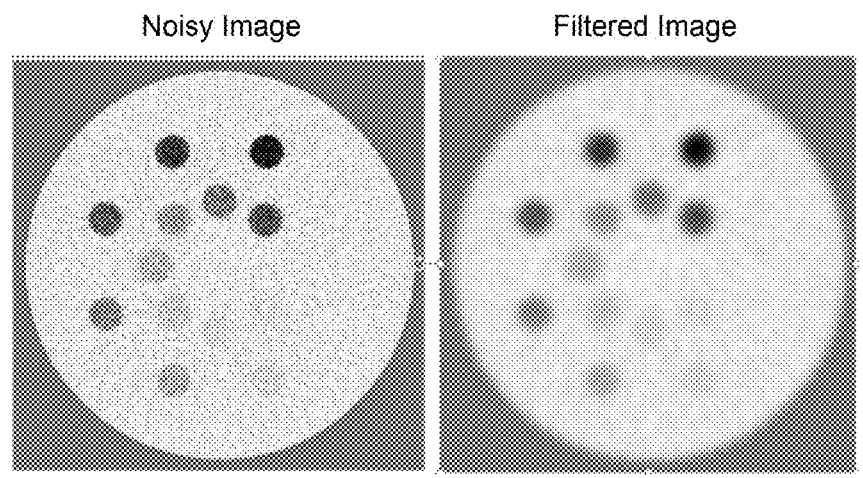
FIG. 6B shows noisy and filtered images in the uncorrelated basis corresponding to the larger eigenvalue of the covariance matrix, according to an isotropic denoising implementation.

FIG. 6B shows simulated results for a second material basis of a noisy image and a filtered image, using an isotropic quadratic regularization.

Figure 7A:
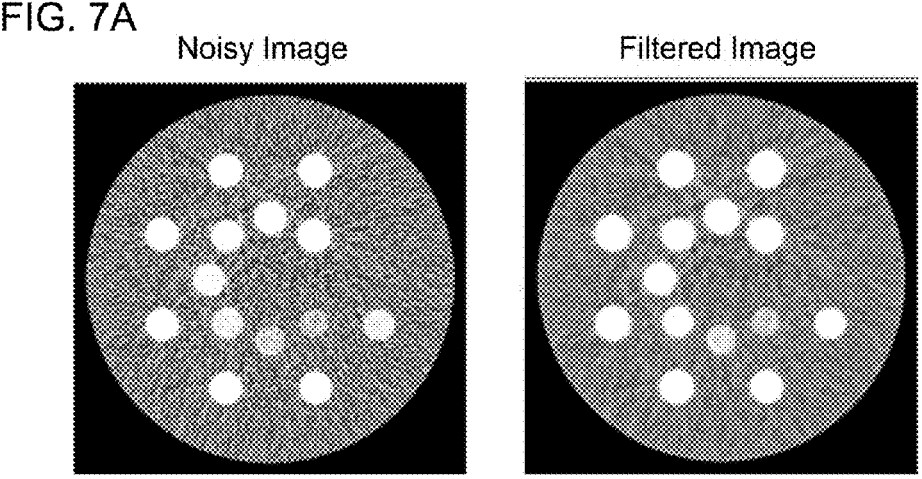
FIG. 7A shows noisy and filtered images for a mono-energetic image corresponding to an X-ray energy of 50 keV, according to an isotropic denoising implementation.
Figure 7B:
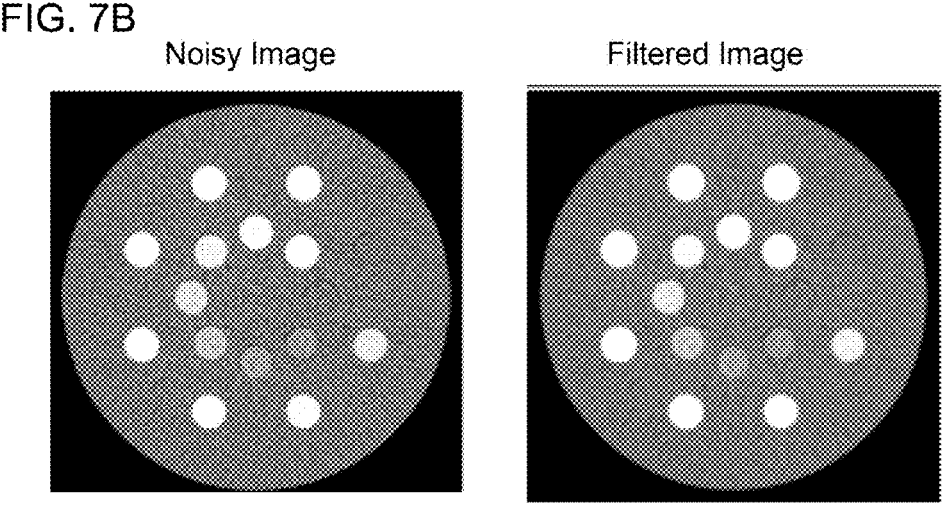
FIG. 7B shows noisy and filtered images for a mono-energetic image corresponding to an X-ray energy of 75 keV, according to an isotropic denoising implementation.
Figure 7C:
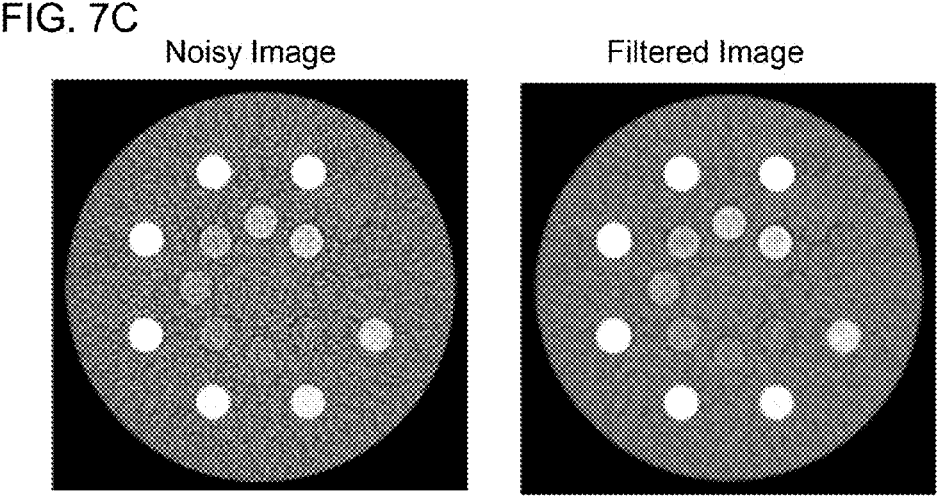
FIG. 7C shows noisy and filtered images for a mono-energetic image corresponding to an X-ray energy of 135 keV, according to an isotropic denoising implementation.

FIGS. 7A, 7B, and 7C show mono-energetic images for X-ray energies of 50 keV, 75 keV, and 135 keV respectively, derived from the images in FIGS. 6A and 6B. FIGS. 7A, 7B, and 7C respectively show noisy images on the left and filtered images on the right. The filtered images were obtained using an isotropic quadratic regularization.

Figure 8A:
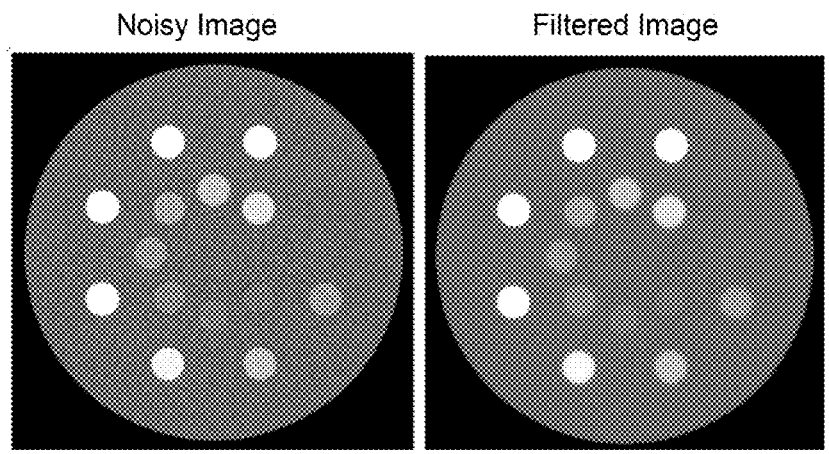
FIG. 8A shows noisy and filtered images in the uncorrelated basis corresponding to the smaller eigenvalue of the covariance matrix, according to an anisotropic denoising implementation.

FIG. 8A shows simulated results for a first material basis of a noisy image and a filtered image, using an anisotropic quadratic regularization.

Figure 8B:
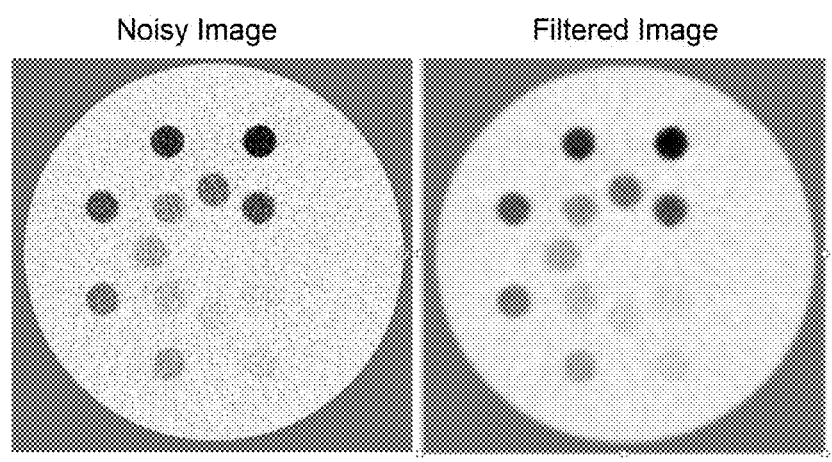
FIG. 8B shows noisy and filtered images in the uncorrelated basis corresponding to the larger eigenvalue of the covariance matrix, according to an anisotropic denoising implementation.

FIG. 8B shows simulated results for a second material basis of a noisy image and a filtered image, using an anisotropic quadratic regularization.

Figure 9A:
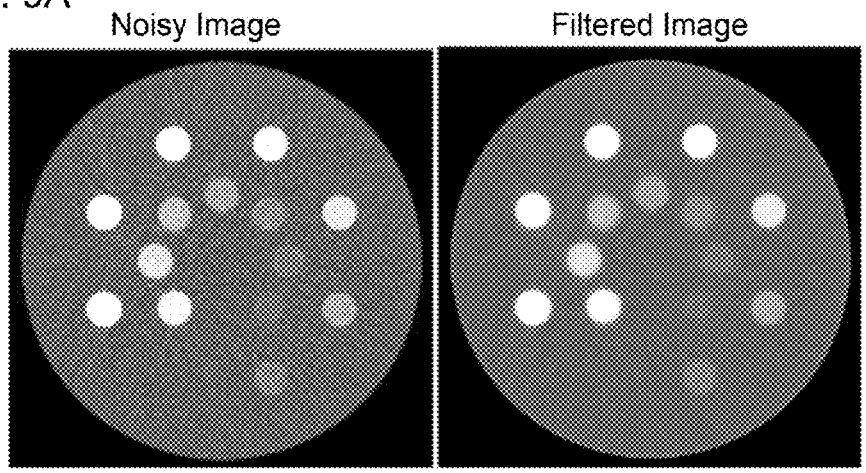
FIG. 9A shows noisy and filtered images for a mono-energetic image corresponding to an X-ray energy of 50 keV, according to an anisotropic denoising implementation.
Figure 9B:
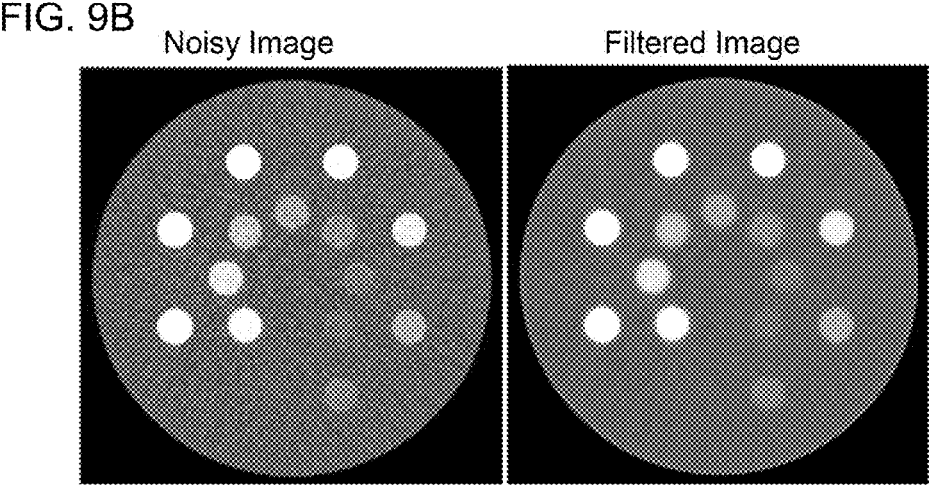
FIG. 9B shows noisy and filtered images for a mono-energetic image corresponding to an X-ray energy of 75 keV, according to an anisotropic denoising implementation.
Figure 9C:
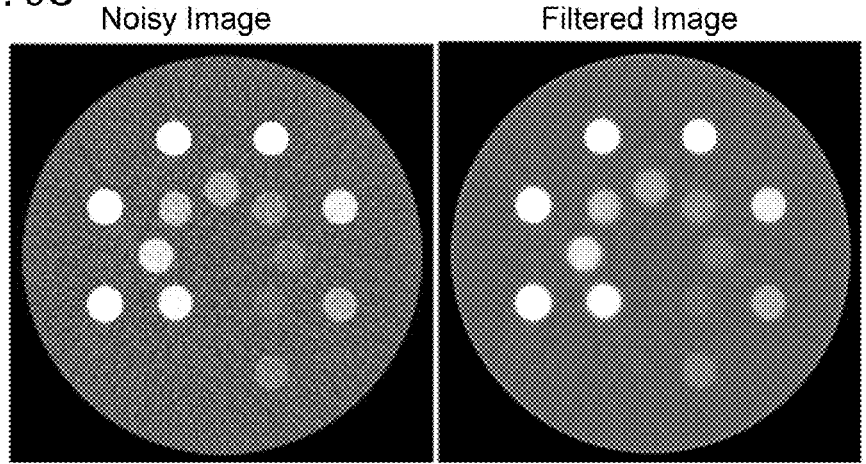
FIG. 9C shows noisy and filtered images for a mono-energetic image corresponding to an X-ray energy of 135 keV, according to an anisotropic denoising implementation.

FIGS. 9A, 9B, and 9C show mono-energetic images for X-ray energies of 50 keV, 75 keV, and 135 keV respectively, derived from the images in FIGS. 8A and 8B. FIGS. 9A, 9B, and 9C respectively show a noisy image and a filtered image. The filtered images were obtained using an anisotropic quadratic regularization.

Figure 10:
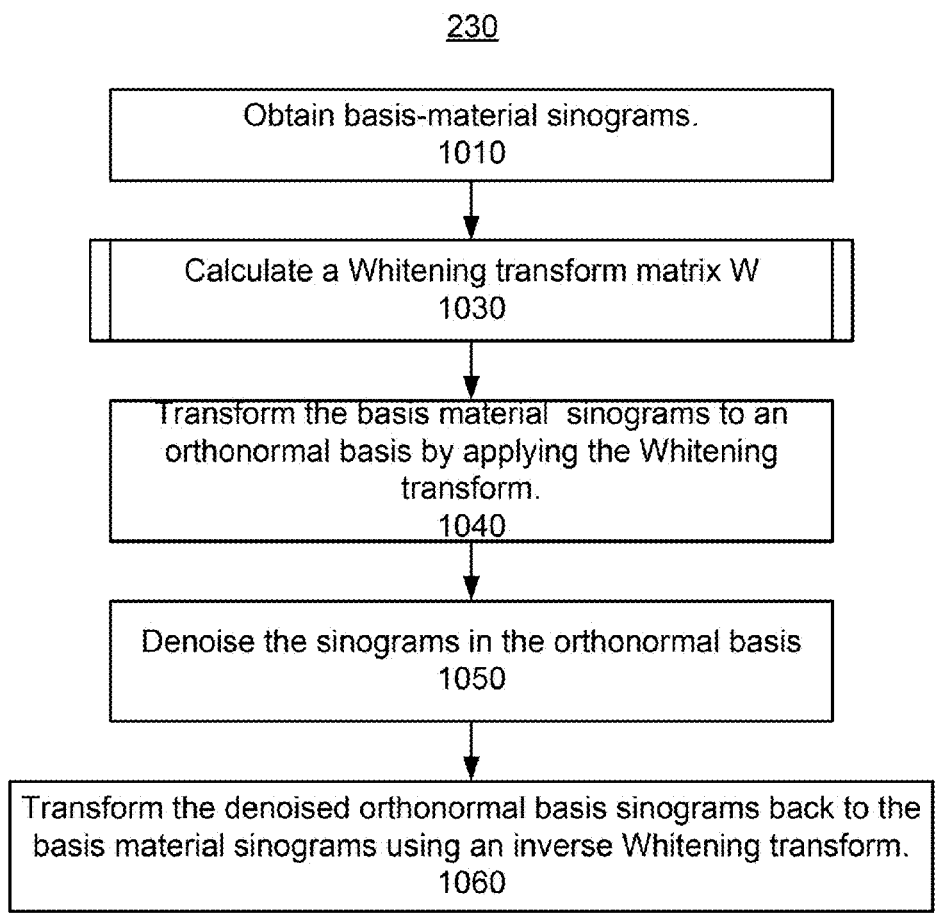
FIG. 10 shows a flow diagram of a process to denoise material-component sinograms using a whitening transform.

FIG. 10 shows a flow diagram of process 230, according to one implementation.

In step 1010 of method 230, the material-component images are obtained.

In process 1030 of method 230, a whitening transform W is calculated in a similar manner to the whitening transform in process 330, except the covariance matrix is between the material-component sinograms $g^{(1)}(X,Y,\theta)$ and $g^{(2)}(X,Y,\theta)$.

In step 1040 of method 230, the whitening transform is calculated, similar to step 340. The whitening transform is calculated as $$W = \Lambda^{-1/2} \Phi^T,$$

and the material-component sinograms $g^{(m)}(X,Y,\theta)$ can be transformed to uncorrelated-basis images $gu^{(m)}(X,Y,\theta)$ according to $$\begin{bmatrix} gu^{(1)}(X,Y,\theta) \\ gu^{(2)}(X,Y,\theta) \end{bmatrix} = \begin{bmatrix} W_{11} & W_{12} \\ W_{21} & W_{22} \end{bmatrix} \begin{bmatrix} gu^{(1)}(X,Y,\theta) \\ gu^{(2)}(X,Y,\theta) \end{bmatrix}.$$

In step 1050 of method 230, denoising is applied to the uncorrelated-basis sinograms, similar to step 350 of method 250.

In step 1060 of method 230, the denoised imaged in the uncorrelated basis are transformed back into the material-component basis using an inverse of the whitening transform, similar to step 360 of method 250.

Figure 11A:
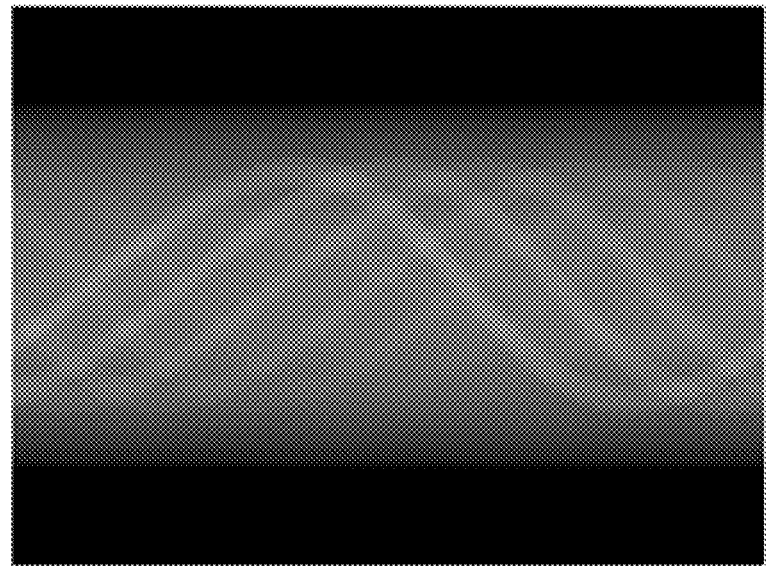
FIG. 11A shows a noisy sinogram image in the uncorrelated basis corresponding to the smaller eigenvalue of the covariance matrix.

FIG. 11A shows a simulated sinogram in the uncorrelated basis after the whitening transformation, but prior to denoising. The sinogram in FIG. 11A corresponds to the smaller eigenvalue of the covariance matrix.

Figure 11B:
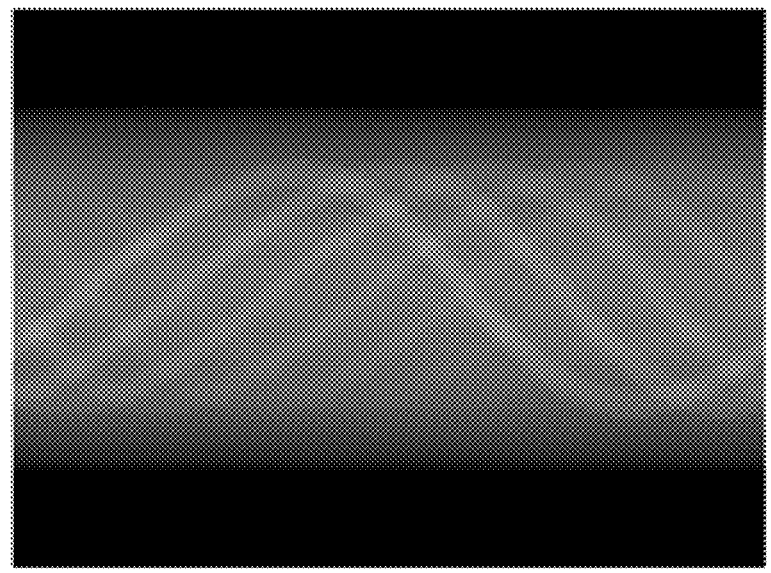
FIG. 11B shows a filtered sinogram image in the uncorrelated basis corresponding to the smaller eigenvalue of the covariance matrix.

FIG. 11B shows the simulated sinogram from FIG. 11A after denoising.

Figure 12A:
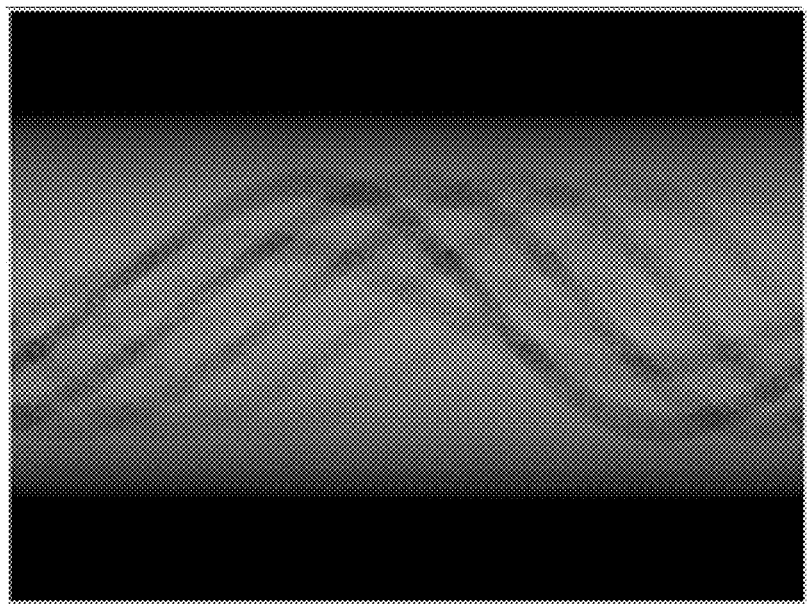
FIG. 12A shows a noisy sinogram in the uncorrelated basis corresponding to the larger eigenvalue of the covariance matrix.

FIG. 12A shows a simulated sinogram in the uncorrelated basis after the whitening transformation, but prior to denoising. The sinogram in FIG. 12A corresponds to the larger eigenvalue of the covariance matrix.

Figure 12B:
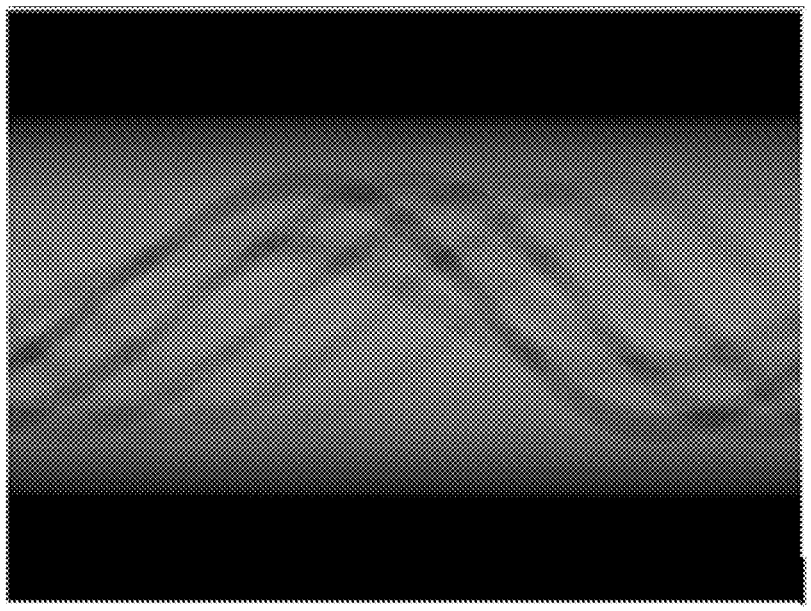
FIG. 12B shows a filtered sinogram in the uncorrelated basis corresponding to the larger eigenvalue of the covariance matrix.

FIG. 12B shows the simulated sinogram from FIG. 12A after denoising.

The denoising in FIGS. 11B and 12B can be performed using an iterative PWLS algorithm having a regularization term that is either quadratic or non-quadratic and that is isotropic or anisotropic and edge preserving, for example.

Figure 13A:
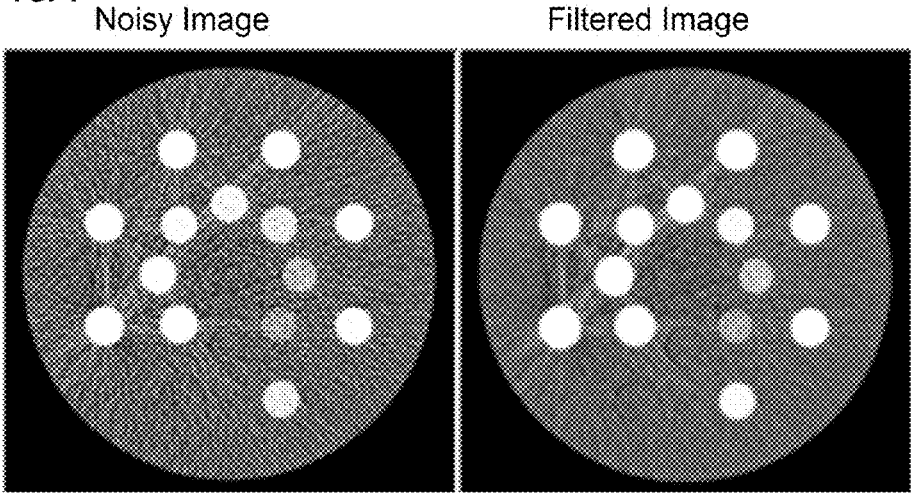
FIG. 13A shows noisy and filtered images for a mono-energetic image corresponding to an X-ray energy of 50 keV, according to a sinogram denoising implementation.
Figure 13B:
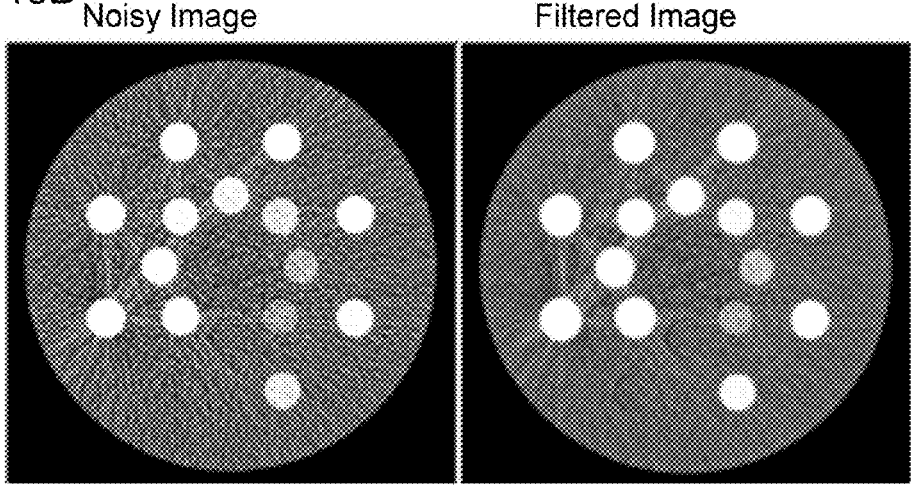
FIG. 13B shows noisy and filtered images for a mono-energetic image corresponding to an X-ray energy of 75 keV, according to a sinogram denoising implementation.
Figure 13C:
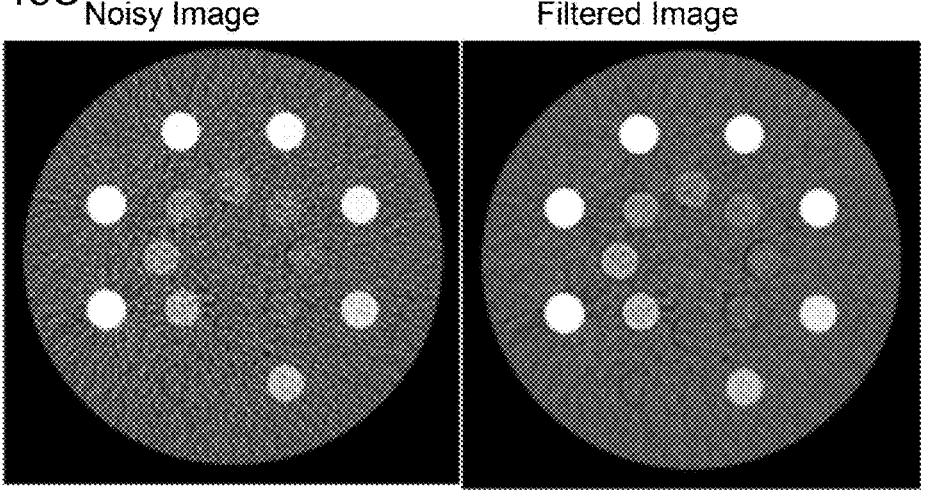
FIG. 13C shows noisy and filtered images for a mono-energetic image corresponding to an X-ray energy of 135 keV, according to a sinogram denoising implementation.

FIGS. 13A, 13B, and 13C show mono-energetic images for X-ray energies of 50 keV, 75 keV, and 135 keV respectively. The images shown in FIGS. 13A, 13B, and 13C are derived from reconstructed images that were reconstructed from the sinograms in FIGS. 11A, 11B, 12A, and 12B. FIGS. 13A, 13B, and 13C respectively show noisy images on the left and filtered images on the right.

FIG. 14 shows a computed tomography (CT) scanner having both energy-integrating detectors arranged in a third-generation geometry and PCDs arranged in a fourth-generation geometry. Illustrated in FIG. 14 is an implementation for placing the PCDs in a predetermined fourth-generation geometry in combination with a detector unit 103 in a predetermined third-generation geometry in a CT scanner system. The diagram illustrates relative positions among the X-ray source 112, the collimator/filter 114, the X-ray detector 103, and the photon-counting detectors PCD1 through PCDN.

Also shown in FIG. 14 is circuitry and hardware for acquiring, storing, processing, and distributing X-ray projection data. The circuitry and hardware include: a processor 1470, a network controller 1480, a memory 1478, and a data acquisition system 1476.

In one alternative implementation, the CT scanner includes PCDs but does not include the energy-integrating detector unit 103.

As the X-ray source 112 and the detector unit 103 are housed in a gantry 1440 and rotate around circular paths 110 and 130 respectively, the photon-counting detectors PCDs and the detector unit 103 respectively detects the transmitted X-ray radiation during data acquisition. The photon-counting detectors PCD1 through PCDN intermittently detect the X-ray radiation that has been transmitted and individually output a count value representing a number of photons, for each of the predetermined energy bins. On the other hand, the detector elements in the detector unit 103 continuously detect the X-ray radiation that has been transmitted and output the detected signals as the detector unit 103 rotates. In one implementation, the detector unit 103 has densely placed energy-integrating detectors in predetermined channel and segment directions on the detector unit surface.

In one implementation, the X-ray source 112, the PCDs and the detector unit 103 collectively form three predetermined circular paths that differ in radius. At least one X-ray source 112 rotates along a first circular path 110 while the photon-counting detectors are sparsely placed along a second circular path 120. Further, the detector unit 103 travels along a third circular path 130. The first circular path 110, second circular path 120, and third circular path 130 can be determined by annular rings that are rotatably mounted to the gantry 1440.

There are other alternative embodiments for placing the photon-counting detectors in a predetermined fourth-generation geometry in combination with the detector unit in a predetermined third-generation geometry in the CT scanner. Several alternative embodiments of the X-ray CT Scanner as described in U.S. patent application Ser. No. 13/0,291,097, herein incorporated by reference in its entirety.

In one implementation, the X-ray source 112 is optionally a single energy source. In another implementation, the X-ray source 112 is configured to perform a kV-switching function for emitting X-ray radiation at a predetermined high-level energy and at a predetermined low-level energy. In still another alternative embodiment, the X-ray source 112 is a single source emitting a broad spectrum of X-ray energies. In still another embodiment, the X-ray source 112 includes multiple X-ray emitters with each emitter being spatially and spectrally distinct.

The detector unit 103 can use energy integrating detectors such as scintillation elements with photo-multiplier tubes or avalanche photo-diodes to detect the resultant scintillation photons from scintillation events resulting from the X-ray radiation interacting with the scintillator elements. The scintillator elements can be crystalline, an organic liquid, a plastic, or other know scintillator.

The PCDs can use a direct X-ray radiation detectors based on semiconductors, such as cadmium telluride (CdTe), cadmium zinc telluride (CZT), silicon (Si), mercuric iodide ($HgI_2$), and gallium arsenide (GaAs).

The CT scanner also includes a data channel that routes projection measurement results from the photon-counting detectors and the detector unit 103 to a data acquisition system 1476, a processor 1470, memory 1478, network controller 1480. The data acquisition system 1476 controls the acquisition, digitization, and routing of projection data from the detectors. The data acquisition system 1476 also includes radiography control circuitry to control the rotation of the annular rotating frames 110 and 130. In one implementation data acquisition system 1476 will also control the movement of the bed 116, the operation of the X-ray source 112, and the operation of the X-ray detectors 103. The data acquisition system 1476 can be a centralized system or alternatively it can be a distributed system. In an implementation, the data acquisition system 1476 is integrated with the processor 1470. The processor 1470 performs functions including reconstructing images from the projection data, pre-reconstruction processing of the projection data, and post-reconstruction processing of the image data. The processor 1470 also performs the functions and methods described herein.

The pre-reconstruction processing of the projection data can include correcting for detector calibrations, detector nonlinearities, polar effects, noise balancing, and material decomposition.

Post-reconstruction processing can include filtering and smoothing the image, volume rendering processing, and image difference processing as needed. The image reconstruction process can be performed using filtered back projection, iterative image reconstruction methods, or stochastic image reconstruction methods. Both the processor 1470 and the data acquisition system 1476 can make use of the memory 1476 to store, e.g., projection data, reconstructed images, calibration data and parameters, and computer programs.

The processor 1470 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the reconstruction processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display. The display can be an LCD display, CRT display, plasma display, OLED, LED or any other display known in the art.

The memory 1478 can be a hard disk drive, CD-ROM drive, DVD drive, FLASH drive, RAM, ROM or any other electronic storage known in the art.

The network controller 1480, such as an Intel Ethernet PRO network interface card from Intel Corporation of America, can interface between the various parts of the CT scanner. Additionally, the network controller 1480 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. An apparatus, comprising:
    processing circuitry configured to
        obtain material-component data corresponding to a material decomposition of projection data having a plurality of energy components, the projection data representing an intensity of X-ray radiation detected at a plurality of energy-resolving detector elements;
        transform the obtained material-component data to an uncorrelated basis using a whitening transform to generate a plurality of pieces of uncorrelated data, noise of the respective pieces of uncorrelated data being uncorrelated;
        de-noise the generated plurality of pieces of uncorrelated data to generate denoised uncorrelated data; and
        transform the denoised uncorrelated data using an inverse whitening transform to generate denoised material-component data.

2. The apparatus according to claim 1, wherein the processing circuitry is configured to obtain the material-component data, which is one of material-component sinograms and material-component images,
    the material-component sinograms being generated by the material decomposition of the projection data, and
    the material-component images being reconstructed from the material-component sinograms.

3. The apparatus according to claim 1, wherein the processing circuitry is further configured to determine the whitening transform, which includes a whitening-transform matrix, using a covariance matrix of the material-component data.

4. The apparatus according to claim 3, wherein the processing circuitry is further configured to determine the whitening-transform matrix, which includes a matrix product of an eigenvector matrix and a square root of a diagonal eigenvalue matrix, the diagonal eigenvalue matrix and the eigenvector matrix being obtained from an eigenvalue decomposition of the covariance matrix.

5. The apparatus according to claim 3, wherein the processing circuitry is further configured to determine the whitening-transform matrix, which includes
    a first row with values respectively corresponding to absorption coefficients of material components of the material-component data at an X-ray energy corresponding to a minimum standard deviation, and
    a second row orthogonal to the first row.

6. The apparatus according to claim 1, wherein the processing circuitry is further configured to transform the material-component data to the uncorrelated basis in a piecewise manner by transforming patches of the material-component data to the uncorrelated basis using the whitening transform, which is a patchwise-dependent whitening transform.

7. The apparatus according to claim 1, wherein the processing circuitry is further configured to denoise the plurality of pieces of uncorrelated data using a penalized weighted least square (PWLS) denoising method.

8. The apparatus according to claim 7, wherein the processing circuitry is further configured to denoise the plurality of pieces of uncorrelated data using the PWLS denoising method, which uses one of an isotropic quadratic regularization and an anisotropic quadratic regularization.

9. The apparatus according to claim 1, wherein the processing circuitry is further configured to denoise the plurality of pieces of uncorrelated data using different denoising parameters between components of the plurality of pieces of uncorrelated data to make noise in the denoised material-component data more uniform as a function of an X-ray energy.

10. The apparatus according to claim 1, wherein the material-component data is material-component images, and
the processing circuitry is further configured to generate the material-component images by
obtaining the projection data,
performing material decomposition of the projection data to generate material-component sinograms, and
reconstructing, for each material-component sinogram, a corresponding material-component image.

11. The apparatus according to claim 1, wherein the material-component data is material-component sinograms, and
the processing circuitry is further configured to generate material-component images from the material-component sinograms by reconstructing, for each material-component sinogram of the denoised material-component data, a corresponding material-component image of the material-component images.

12. An apparatus, comprising:
an X-ray source radiating X-rays;
a plurality of detector elements each configured to
detect a plurality of energy components of the X-rays that are radiated from the X-ray source,
generate projection data representing an intensity of X-ray radiation detected at a plurality of energy-resolving detector elements; and
processing circuitry configured to
obtain material-component data corresponding to a material decomposition of the projection data having a plurality,
transform the obtained material-component data to an uncorrelated basis using a whitening transform to generate a plurality of pieces of uncorrelated data, noise of the respective pieces of uncorrelated data being uncorrelated,
denoise the generated plurality of pieces of uncorrelated data to generate denoised uncorrelated data, and
transform the denoised uncorrelated data using an inverse whitening transform to generate denoised material-component data.

13. The apparatus according to claim 12, wherein the processing circuitry is configured to obtain the material-component data, which is material-component sinograms, and
the processing circuitry further configured to
perform the material decomposition of the projection data to generate the material-component data, and
reconstruct, using the denoised material-component material, material-component images.

14. The apparatus according to claim 13, wherein the processing circuitry further configured to
transform the material-component images to an uncorrelated basis using the whitening transform to generate uncorrelated images,
denoise the uncorrelated images, and
transform the denoised uncorrelated images using the inverse whitening transform to generate denoised material-component images.

15. The apparatus according to claim 12, wherein the material-component data is material-component images, and
the processing circuitry further configured to
perform the material decomposition of the projection data to generate material-component sinograms, and
reconstruct, using the material-component sinograms, the material-component data.

16. A method, comprising:
obtaining material-component data corresponding to a material decomposition of projection data having a plurality of energy components, the projection data representing an intensity of X-ray radiation detected at a plurality of energy-resolving detector elements;
transforming the obtained material-component data to an uncorrelated basis using a whitening transform to generate a plurality of pieces of uncorrelated data, noise of the respective pieces of uncorrelated data being uncorrelated;
denoising the generated plurality of pieces of uncorrelated data to generate denoised uncorrelated data; and
transforming the denoised uncorrelated data using an inverse whitening transform to generate denoised material-component data.

17. The method according to claim 16, wherein the material-component data is one of material-component sinograms and material-component images.

18. The method according to claim 17, wherein
the material-component sinograms are generated by the material decomposition of the projection data, and
the material-component images are reconstructed using the material-component sinograms.

19. The method according to claim 16, further comprising:
determining the whitening transform, which includes a whitening-transform matrix, using a covariance matrix of the material-component data.

20. A non-transitory computer readable storage medium including executable instruction, wherein the instructions, when executed by circuitry, cause the circuitry to perform the method according to claim 16.

* * * * *